(12) United States Patent
Al-Babili et al.

(10) Patent No.: US 9,326,510 B2
(45) Date of Patent: *May 3, 2016

(54) STRIGOLACTONE ANALOGUES AND THEIR USE

(71) Applicant: KING ABDULLAH UNIVERSITY OF SCIENCE AND TECHNOLOGY, Thuwal (SA)

(72) Inventors: Salim Al-Babili, Thuwal (SA); Adrian Alder, Bern (CH)

(73) Assignee: KING ABDULLAH UNIVERSITY OF SCIENCE AND TECHNOLOGY, Thuwal (SA)

( * ) Notice: Subject to any disclaimer, the term of this patent is extended or adjusted under 35 U.S.C. 154(b) by 0 days.

This patent is subject to a terminal disclaimer.

(21) Appl. No.: 14/645,823

(22) Filed: Mar. 12, 2015

(65) Prior Publication Data

US 2015/0250170 A1 Sep. 10, 2015

Related U.S. Application Data

(63) Continuation of application No. 14/113,794, filed as application No. PCT/EP2012/001766 on Apr. 25, 2012, now Pat. No. 8,980,795.

(30) Foreign Application Priority Data

Apr. 28, 2011 (EP) .................... 11003470

(51) Int. Cl.
*C12P 17/04* (2006.01)
*A01N 43/08* (2006.01)
*C07D 307/58* (2006.01)
*C12P 5/00* (2006.01)

(52) U.S. Cl.
CPC ............. *A01N 43/08* (2013.01); *C07D 307/58* (2013.01); *C12P 5/002* (2013.01); *C12P 17/04* (2013.01)

(58) Field of Classification Search
CPC ....... C07D 307/58; C12P 17/04; A01N 43/08
See application file for complete search history.

(56) References Cited

U.S. PATENT DOCUMENTS 8,980,795 B2 * 3/2015 Al-Babili et al. ............ 504/299

FOREIGN PATENT DOCUMENTS

| WO | WO 2008/152091 | 12/2008 |
| WO | WO 2008/152092 | 12/2008 |

OTHER PUBLICATIONS

Wigchert et al., caplus an 2012:1449363, 2012.*
Zwanenburg et al., caplus an 2009:558586, 2009.*
Mangnus, 2012, 2012:1449008.*
Lattmann et al., 2004, 2004:1059333.*
International Preliminary Report on Patentability received in connection with international application No. PCT/EP2012/001766; Oct. 23, 2013.
International Search Report received in connection with international application No. PCT/EP2012/001766; Jan. 23, 2013.
Brooks, Dee W. et al: "Strigol: total synthesis and preparation of analogs", ACS Symposium Series, vol. 268(Chem. Allelopathy), 437-444 (1985).
Chen et al., Science in China, Series C, Life Sciences, "Strigolactones are a new-defined class of plant hormones which inhibit shoot branching and mediate the interaction of plant-AM fungi and plant-parasitic weeds", Gordon and Breach, Amsterdam, NL, vol. 52(8), (2009), pp. 693-700.
Colby, S. R., "Calculating synergistic and antagonistic response of herbicide combinations". Weeds, vol. 15, pp. 20-22 (1967).
Ernst et al., "The vapor pressure of eleven organic compounds"; J. of the American Chemical Society (1948), 70, 2582-3; CAPLUS AN 1948:40543.
Fu et al., "Efficient Preparation of 4-iodofuran-2(5H)-ones by Iodolactonisation of 2,3-Allenoates with $I_2$", Eur. J. Org. Chem., 3942-3945,(2005).
Johnsson et al: "The Preparation of Synthetic Analogues of Strigol", J.Chem.Soc. Perkin Trans. I. No. 6, (Jan. 1, 1981), pp. 1734-1743.
Kondo et al., "Synthesis and Seed Germination Stimulating Activity of Some Imino Analogs of Strigolactones", Biosci. Biotechnol. Biochem., vol. 71, No. 11, pp. 2781-2787 (2007).
Lin et al., The Plant Cell; "DWARF27, an Iron-Containing Protein Required for the Biosynthesis of Strigolactones, Regulates Rice Tiller Bud Outgrowth", Am. Soc. of Plant Biologists, vol. 21, No. 5, May 2009, pp. 1512-1525.

(Continued)

*Primary Examiner* — Sun Jae Yoo
(74) *Attorney, Agent, or Firm* — The Marbury Law Group, PLLC (57) ABSTRACT

Novel compounds of formula (I)

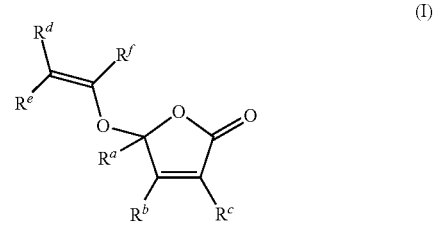

their use as germination trap for parasitic weeds, for the regulation of branching, tillering and root development, for enhancement of cambium growth, for the regulation of hyphal growth of mycorrhizal fungi and compositions comprising compounds of formula (I) and insecticides and/or fungicides.

19 Claims, No Drawings

(56) References Cited

OTHER PUBLICATIONS

Ma et al., "A palladium catalyzed efficient synthesis of γ-methylene-α,β-unsaturated γ-lactones via cyclization of 3,4-alkadienoic acids", Tetrahedron, 61, (2005) pp. 9896-9901.

Mangnus et al., "Structural modifications of strigol analogs. Influence of the B and C rings on the bioactivity of the germination stimulant GR24", J. Agrif. Food Chem., vol. 40(7), (1992) 1222-1229.

* cited by examiner

STRIGOLACTONE ANALOGUES AND THEIR USE

The present invention relates to novel compounds and to the uses thereof for combatting or controlling parasitic weeds and for the regulation of certain plant properties and mycorrhizal fungi-plant interaction.

In the recent past, a new class of carotenoid-derived compounds have been intensively studied and are commonly referred to as strigolactones. Strigolactones have been identified in the root exudates of plants and are known to stimulate seed germination of parasitic plants, such as *Striga* and *Orobanche* (which are amongst the main agricultural pest worldwide), and to induce hyphal growth of arbuscular mycorhizal (AM) fungi that form symbiotic structures (arbuscules) with the majority of land plants. More recently strigolactones have been identified as plant hormones regulating branching and cambium growth.

Figure 1:
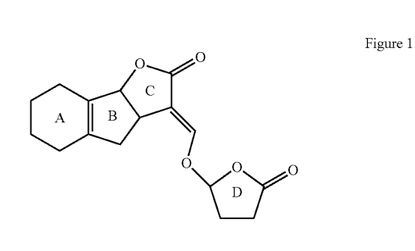

As shown in FIG. 1, the common feature of the strigolactones is the combination of a tricyclic lactone comprising rings A, B and C connected to a butenolide group (D) that also represents a lactone.

Figure 1

Rings A, B and D may carry a variety of substituents and may underlie different modifications, but all strigolactones share the common basic structure shown in FIG. 1.

The infection with *Striga* and orobanchaceae is responsible for annual losses for farmers of billions of dollars all over the world. Around two third of the area for cereal crop production in Africa are infected with *Striga* varieties. Alectra, a member of the orobanchaceae affects dicotyledonous crops in large parts of Europe and North America and is responsible for significant yield losses.

As shown in FIG. 1, the tricyclic lactone comprising rings A, B and C and the butenolide D are connected through an enol ether bridge. Due to this specific structure, all natural strigolactones are very susceptible to nucleophilic attack (hydrolysis) and thus unstable in aqueous systems. Furthermore, their solubility in aqueous systems is normally very low.

Furthermore, the compounds in accordance with FIG. 1 comprise an enone structural element built by the double bond between rings C and D and the keto group in ring C. This substructure also has a detrimental influence on the stability and properties of the said compounds. This enone structure has hitherto been considered indispensible to achieve the desired activity.

In view of their great potential for the so-called suicide germination of parasitic weeds (this means the germination in the absence of a suitable host plant which will ultimately lead to the death of the parasitic plant) thorough investigations have been undertaken to determine the minimum structural requirements necessary to maintain the desired germination stimulating activity.

Strigolactones have also been shown to play a role in establishing symbiotic arbuscular mycorrhiza (AM), a symbiotic structure formed by plants and soilborne fungi. AM allows plants to obtain water and nutrients from the soil through the hyphae of the fungi and in turn the plants provide the fungi with photosynthates. AM is considered very advantageous for crop yield and represent the most widespread symbiosis on earth. The establishment of AM requires extensive branching of the hyphae, which is induced by root-derived signals commonly referred to as branching factor (BF). Strigolactones play a role in this process. The structural requirements for this desired activity are deemed to be very similar to those for the above mentioned suicide germination of the parasitic weeds.

Finally, it has been shown that strigolactones fulfil the criteria of hormones, i.e. they require a receptor mediating their response, they are active at very low concentrations and they can be transported in the plant over some distance. Various investigations have shown that strigolactones are involved in root and lateral root growth and in photo-morphogenesis. Further, they control the growth of cambium, indicating an important role in wood production.

A number of structural studies have been carried out to get a better understanding of the essential parts in the strigolactone molecule for achieving desired properties as referred to above. The replacement of the A-ring by an aromatic ring leads to the active analogue commonly referred to as GR24. Analogues lacking the A-ring (GR7) or both the A- and B-ring (GR5) still exhibit appreciable, albeit lower activities.

In contrast, omitting of the D-ring or the ABC enol ether results in basically complete loss of the desired activity. An analogue consisting only of a D-ring with an ethoxy group is also inactive. Based on these structure-activity data, it was concluded that an essential minimal requirement is the presence of the structural elements of the D-ring connected with an enone unit via the mentioned enol ether. As mentioned above, this unit, however, causes an inherent low stability of the active compounds in aqueous media combined with a low solubility. This makes their use in applications in the crop protection area difficult.

Zwanenburg et al (J. Agrif. Food Chem. 1992, 40, 1222-1229) describes structural modifications of strigol analogues and analyzes the influence of the B and C rings on the bioactivity. FIG. 2 on page 1225 shows a modified strigol analogue which again comprises an enone substructure involving the carbon atom of the double bond between the butenolide structure and the remainder of the molecule, which is detrimental for the stability of the compounds (as mentioned hereinbefore).

Brooks et al., ACS Symposium Series, 268, 437-444 discloses compounds 30 a and 30 b which again have the undesired enone substructure.

Kondo et al., Biosci. Biotechnol. Biochem. 71, 11, 2781-2787 discloses imino analogues of strigolactones which share inter alia a common structural element of an enone structure as outlined above.

Johnsson et al., J. Chem.Soc. Perkin Trans. I, No. 6, Jan. 1, 1981, pages 1734-1743 describes procedures for the preparation of synthetis analogues of strigol, which share the common structural feature of an enone-substructure as described above.

In Sci. China Ser. C Life Sciences, 2009 52(8), 693-700 the authors describe strigolactone derivatives with rings C and D as shown in FIG. 1 and thus comprising the undesired enone-substructure as outlined above.

Accordingly, there was a need for strigolactone analogues or compounds having similar activity as the strigolactones described in the prior art while at the same time showing enhanced stability in aqueous media.

It was thus an object of the instant invention to provide novel compounds showing beneficial properties similar to those of strigolactones, but having an improved stability, in particular against nucleophilic attack/hydrolysis.

It was a further object of the instant invention to provide beneficial uses for such new compounds in the regulation of certain plant properties.

These objects have been achieved with the novel compounds in accordance with claim 1. Preferred compounds are described in detail hereinafter and are claimed in dependent claims.

The novel compounds in accordance with the instant invention are represented by the general formula I (I)

wherein $R^a$, $R^b$ and $R^c$, independently from each other, represent:

a hydrogen atom, a halogen atom, a nitro group, a cyano group, a formyloxy group, a formylamino group or a carbamate group, a substituent-$R^1$, wherein $R^1$ represents $C_1$-$C_8$-alkyl-, $C_2$-$C_8$alkenyl, $C_2$-$C_8$-alkinyl, $C_3$-$C_8$-cycloalkyl or $C_1$-$C_8$-alkoxy, in each of which the hydrogen atoms may be partly replaced by other groups or atoms, a substituent —$OR^2$, wherein $R^2$ represents a hydrogen atom, $C_1$-$C_8$-alkyl, $C_2$-$C_8$-alkenyl, $C_2$-$C_8$-alkinyl, $C_1$-$C_8$-alkylcarbonyl, $C_1$-$C_8$-alkylaminocarbonyl or $C_1$-$C_8$-alkoxycarbonyl, in each of which the hydrogen atoms may be partly replaced by other groups or atoms a substituent —$NR^3R^4$, wherein $R^3$ and $R^4$, independently from each other, represent a hydrogen atom, $C_1$-$C_8$ alkyl, $C_1$-$C_8$-alkylcarbonyl, $C_1$-$C_8$-halogenoalkylcarbonyl, phenyl or benzyl, in each of which the hydrogen atoms may be partly replaced by other groups or atoms, a substituent —$C(O)$—$R^5$, wherein $R^5$ represents a hydrogen atom, $C_1$-$C_8$-alkyl or $C_1$-$C_8$-alkyloxy, in each of which the hydrogen atoms may be partly replaced by other groups or atoms, —$NH2$, $NHR^5$ or $NR^5R^5$ (where the two substituents $R^5$ may be the same or different, —$NR^5(OH)$, a substituent —$S(O)n$—$R^6$, wherein n is 0, 1 or 2 and $R^6$ represents $C_1$-$C_8$-alkyl in which the hydrogen atoms may be partly replaced by other groups or atoms, —$NH_2$, —$NHR^6$ or $NR^6R^6$ (where the two substituents $R^6$ may be the same or different), or a 4-, 5-, 6- or 7-membered heterocyclic ring comprising up to 4 heteroatoms selected from nitrogen, oxygen or sulfur, where in each of these rings the hydrogen atoms may be partly replaced by other groups or atoms, $R^d$ represents $C_1$-$C_8$alkyl, $C_2$-$C_8$-alkenyl or $C_2$-$C_8$-alkinyl, wherein the hydrogen atoms may be partly replaced by other groups or atoms, $R^e$ represents a substituent $R^1$ as defined above, or —CH=CH—$R^7$, wherein $R^7$ represents a hydrogen atom, $C_1$-$C_8$-alkyl or a 4-, 5- 6- or 7-membered saturated or unsaturated, aromatic or non-aromatic carbocyclic or heterocyclic ring or a fused ring system containing more than one of those rings or $R^d$ and $R^e$ together form a 4-, 5- 6- or 7-membered saturated or unsaturated, aromatic or non-aromatic carbocyclic or heterocyclic ring which may be fused to another saturated or unsaturated, aromatic or non-aromatic carbocyclic or heterocyclic ring with the proviso that the carbon atom carrying substituents $R^d$ and $R^e$ is not part of an enone-structural element, and $R^f$ represents a hydrogen atom, a halogen atom, a nitro group, a cyano group or $C_1$-$C_8$-alkyl-, $C_2$-$C_8$ alkenyl, $C_2$-$C_8$-alkinyl or $C_3$-$C_8$-cycloalkyl.

The compounds of formula I, depending on the number of double bonds, may exist in different isomers and formula I is intended to cover all such isomers and to any mixtures thereof.

Due to the lack of the enone group such as represented by ring C, the stability of the novel compounds of formula I against nucleophilic attack/hydrolysis is improved compared to previously known strigolactones. Despite the lack of the enone substructure which has hitherto been considered indispensible for the desired activity of the strigol analogues, the novel compounds in accordance with the present invention surpirsingly show the desired activity, which is contrary to the expectations of the skilled person in view of the teaching of the prior art.

Preferred novel compounds in accordance with the present invention do not have the enol ether bridge between the butenolide D (lactone) and a ring C—they do not contain a ring C at all but still retain the desired activity to a significant degree. Thus, they lack the structural element which has hitherto been considered indispensible for the germination stimulating activity and other desired properties. This was not to be expected based on prior knowledge.

According to a first preferred embodiment, $R^a$ and $R^b$ are both hydrogen and $R^c$ is a substituent $R^1$, even more preferred $R^c$ is a $C_1$ to $C_8$-alkyl group, in particular a $C_1$-$C_4$alkyl group and most preferred a methyl group.

According to a further preferred embodiment, Re represents a substituent —CH=CH—$R^7$, in which $R^7$ represents a 4- to 7-membered saturated or unsaturated, aromatic or non aromatic carbocyclic or heterocyclic ring or a fused ring system containing more than one of those rings. More preferably $R^7$ is a five- or six membered carbocyclic ring which may be saturated or unsaturated, even more preferably $R^7$ is a cyclohexenyl ring. The ring $R^7$ may be substituted by various substituents and preferably by a hydroxyl group or $C_1$-$C_8$-alkyl, $C_1$-$C_8$-alkoxy or acetyl groups.

Still in another preferred embodiment, Re represents a $C_1$-$C_8$alkyl or a $C_2$-$C_8$-alkenylene group, optionally substituted with a hydroxyl group or a carbonyl group or a cycloalkyl group which itself might be substituted by e.g. one or more alkyl groups.

A particularly preferred group of compounds is represented by the following formulae, wherein the cyclohexenyl or the phenyl ring may optionally be substituted by further methyl or hydroxyl groups.

Most particularly preferred is the following compound (IA)

The novel compounds of formula I can in principle be obtained by a coupling of the butenolide (lactone D) structure with the remaining part of the molecule via an enol ether bridge.

The synthesis of butenolides has been described in the literature extensively so that further details are not necessary here. By way of example reference is made to Tetrahedron 2005, 61, 9896 (S. Ma and F. Yu, relating to the synthesis of γ-methylene-α,β-unsaturated γ-lactones by Pd catalyzed cyclization of 3,4-alkadienoic acids) and C. Fu, S. MA, Eur. J. Org. Chem. 2005, 3942ff, relating to the iodolactonisation of ethyl-2,3-allenoates with Iodine in aqueous MeCN.

The novel compounds of formula I may also be obtained by biochemical synthesis in vitro using heterologously expressed CCD7, CCD8 and DWARF27 enzymes or in vivo by expressing the genes coding for CCD7, CCD8 and DWARF 27 enzymes in a production host. Respective methods are known as such to the skilled man and need not be further explained here. Microorganisms and moss may be mentioned as production hosts.

In the context of the studies leading to the present invention, it was additionally found that the combined activities of the carotinoid cleavage dioxygenases CCD7 and CCD8 lead to an unexpected product (see Example 1).

The further study of the reaction mechanism revealed 9-cis-carotenoids, e.g. 9-cis-β-carotene, as precursors that are cleaved by CCD7 enzymes at the 9',10' double bond leading to 9-cis-apo-10'-carotenals, e.g. 9-cis-β-apo-10'-carotenal. Incubation of CCD8 enzymes with 9-cis-β-apo-10'-carotenal or combined CCD7/CCD8 assays with 9-cis-β-carotene lead to the compound with the structure IA (IA)

i.e. a particularly preferred compound in accordance with the instant invention.

This product of combined CCD7/CCD8 activity and the identification of 9-cis-β-carotene as substrate give rise to the assumption that the biosynthetic pathway leading to 5-deoxystrigol (which is proposed to be the precursor of all strigolactones) might be simpler than initially supposed.

In the course of the mechanistic studies, it was also found by the inventors that the protein DWARF-27, which is known to be involved in the pathway to strigolactones in rice, is the isomerase required to produce the precursor 9-cis-β-carotene from all-trans-β-carotene and thus a further aspect of the invention relates to the use of DWARF-27 for isomerising all-trans-carotenes, e.g. for producing 9-cis-β-carotene and other 9-cis-carotenes from their corresponding all-trans-isomers.

As already referred to above, the compounds of formula I and in particular the compound obtained through the CCD7/CCD8 activity show properties and behaviour like strigolactones but without the need of having an enone structure coupled to a butenolide, which, as mentioned leads to an inherent instability against nucleophilic attack.

Different strategies, e.g. sanitation and hand weeding, crop rotation, improving soil fertility, soil treatment by fumigation and solarization, biological control, the use of selective herbicides, the use of herbicide-resistant maize, chemicals inhibiting attachment (Strigaway®; BASF SE) and suicidal germination and breeding for resistance, have been employed to control root parasites. In general, these control strategies target either pre-attachment or post-attachment life-cycle stages of parasitic plants. Since root parasites affect host development immediately after attachment and cause important damage prior to parasite emergence, control strategies, which target pre-attachment stages of the host-parasite interaction, are preferred. Being the first critical step in the interaction makes germination an important target for improved control measures. One advantage of this approach is that the inducing molecules are common to both Striga and Orobanche spp. Indeed, several control strategies based on the germination stimulants have already been developed.

The compounds in accordance with the instant invention can be used as synthetic analogues to induce the germination of the seeds of the parasitic weeds. If these compounds are applied in the absence of a suitable host plant for the weed, the seeds will germinate and the parasitic weed will finally die due to the lack of a suitable host. For example, the compounds in accordance with the instant invention may be used in the seed treatment of seeds of non-hosts of the parasitic weeds, which may be used prior to planting the desired crop. Alternatively, one could think of using compounds in accordance with the instant invention together with a known herbicide for the parasitic weeds for the treatment of seeds of the utility crops prior to transferring such seeds to the soil. If the crop itself is resistant against the herbicide, the compounds in accordance with the instant invention would trigger the germination of the parasitic weeds which would then be killed by the herbicide without negatively affecting the crop plant. All these different possibilities are included in the term germination trap and same should be interpreted accordingly.

The compounds in accordance with the instant invention are also useful to regulate, respectively to enhance, the hyphal growth of symbiotic mycorrhizal fungi, which is a highly desirable symbiosis as same increases crop yields. This has in particular been observed in arbuscular mycorrhizal fungi like e.g. Gigaspora rosea.

A third beneficial usability of the compounds in accordance with the instant invention is the regulation, respectively enhancement of cambium growth, which is very important in wood production.

The compounds in accordance with the instant invention are also useful for the regulation of branching, tillering and root development of plants.

The aerial plant architecture of aboveground shoots is determined by the pattern of shoot branching. The first step in shoot branching is the generation of axillary buds. Their development is mainly regulated by genetics, but plants are able to modify their behaviour in response to environmental changes. The compounds in accordance with the instant invention are useful to control the shoot branching of crops in a desired manner by applying these compounds to the crop in question.

Tiller is a stem produced at the base of grass plants and tillering refers to the production of such tillers, which process is strongly influenced by the soil status. Tillering in rice (Oryza sativa L.) is an important agronomic trait for grain production, and also a model system for the study of branching in monocotyledonous plants. Rice tiller is a specialized grain-bearing branch that is formed on the unelongated basal internode and grows independently of the mother stem (culm) by means of its own adventitious roots. The compounds of the instant invention can be used to regulate tillering in rice, thus increasing yields.

Furthermore, it has been found that compositions comprising at least one compound of formula I and at least one insecticide and/or fungicide known in the art show surprisingly increased efficiency for combating or controlling pests or fungi, in particular fungi detrimentally affecting plants.

Processes for the treatment of fungi within or attached to the human body or within animals, to the extent same would constitute a therapeutic treatment of humans or animals, are excluded.

These compositions may provide a synergistic effect, which allows the reduction of the amount of chemicals spread and a reduction of the treatment costs.

When used herein, the term synergistic effect means an efficacy of a new combination of more than one compound exceeding the efficacy calculated in accordance with the formula of Colby (Weeds 1967, 15, pages 20-22). This formula reads $$E=x+y-(x*y)/100$$

in which E represents the expected efficiency (degree of inhibition of disease or pest) for the combination of two compounds at defined doses, x is the percentage of inhibition observed for the pest or disease by the first compound of the combination (at a defined dose) and y is the respective efficiency for the second compound of the combination. When the observed efficiency is higher than the expected efficiency according to this formula, this constitutes a synergistic effect.

The compositions containing at least one compound of formula I in accordance with the instant invention and at least one insecticide or fungicide known in the art show such improvement compared to the single compounds in plant growth, vigor or yield of plants or crops or insecticidal or fungicidal effect.

The weight ratio of the compounds in accordance with the instant invention to the known insecticides or fungicides may cover a broad range of from 0.5:1 to $1:10^{14}$, preferably of from $1:10^2$ to $1:10^8$, and more preferably of from $1:10^3$ to $1:10^7$, i.e. the content of the known insecticide or fungicide is usually much higher than the concentration of the compounds in accordance with the instant invention.

Suitable insecticides are known to the skilled man and have been described in the literature. They are generally classified in accordance with their mode of action (to the extent same is known) as acetylcholione receptor agonists or antagonists, acetylcholinesterase inhibitors, sodium channel modulators or sodium channel blockers, GABA-gated chloride channel antagonists, ecdysone agonists/disruptors, chloride channel activators, semicarbazones, juvenile hormone mimetics, acetylcholine receptor modulators, neirostoxin analogues, inhibitors of lipid biosynthesis, decouplers of oxidative phosphorylation, electron transport inhibitors (site I, site II and site III), carboxamides, inhibitors of ATP-ase, inhibitors of oxidative phosphorylation, inhibitors of chitine biosynthesis, microbial disruptors of the intestinal membrane or ryanodin receptor antagonists. Furthermore, so called biologicals, hormones or pheromones are known to the skilled man and there are also insecticides which are commercially used the mode of action however is not yet fully clarified.

The skilled man knows suitable insecticides of the aforementioned categories suitable for the mixture compositions in accordance with the instant invention. A good overview, including preferred insecticidal compounds is given in WO 2008/152091, to which reference is made in this regard.

Preferred insecticides useful in the compisitions in accordance with the present invention are listed below:

organo(thio)phosphates: acephate, azamethiphos, azinphos-methyl, chlorpyrifos, chlorpyrifos-methyl, chlorfenvinphos, diazinon, dichlorvos, dicrotophos, dimethoate, disulfoton, ethion, fenitrothion, fenthion, isoxathion, malathion, methamidophos, methidathion, methyl-parathion, mevinphos, monocrotophos, oxydemeton-methyl, paraoxon, parathion, phenthoate, phosalone, phosmet, phosphamidon, phorate, phoxim, pirimiphos-methyl, profenofos, prothiofos, sulprophos, tetrachlorvinphos, terbufos, triazophos, trichlorfon;

carbamates: alanycarb, aldicarb, bendiocarb, benfuracarb, carbaryl, carbofuran, carbosulfan, fenoxycarb, furathiocarb, methiocarb, methomyl, oxamyl, pirimicarb, propoxur, thiodicarb, triazamate;

pyrethroids: allethrin, bifenthrin, cyfluthrin, cyhalothrin, cyphenothrin, cypermethrin, alpha-cypermethrin, beta-cypermethrin, zeta-cypermethrin, deltamethrin, esfenvalerate, etofenprox, fenpropathrin, fenvalerate, imiprothrin, lambda-cyhalothrin, permethrin, prallethrin, pyrethrin I and II, resmethrin, silafluofen, tau-fluvalinate, tefluthrin, tetramethrin, tralomethrin, transfluthrin, profluthrin, dimefluthrin;

insect growth regulators: a) chitin synthesis inhibitors: benzoylureas: chlorfluazuron, cyramazin, diflubenzuron, flucycloxuron, flufenoxuron, hexaflumuron, lufenuron, novaluron, teflubenzuron, triflumuron; buprofezin, diofenolan, hexythiazox, etoxazole, clofentazine; b) ecdysone antagonists: halofenozide, methoxyfenozide, tebufenozide, azadirachtin; c) juvenoids: pyriproxyfen, methoprene, fenoxycarb; d) lipid biosynthesis inhibitors: spirodiclofen, spiromesifen, spirotetramat;

nicotinic receptor agonists/antagonists compounds: clothianidin, dinotefuran, flupyradifurone, imidacloprid, thiamethoxam, nitenpyram, acetamiprid, thiacloprid, 1-2-chloro-thiazol-5-ylmethyl)-2-nitrimino-3,5-dimethyl-[1,3,5]triazinane;

GABA antagonist compounds: endosulfan, ethiprole, fipronil, vaniliprole, pyrafluprole, pyriprole, 5-amino-1-(2,6-dichloro-4-methyl-phenyl)-4-sulfinamoyl-1H-pyrazole-3-carbothioic acid amide;

macrocyclic lactone insecticides: abamectin, emamectin, milbemectin, lepimectin, spinosad, spinetoram;

mitochondrial electron transport inhibitor (METI) I acaricides: fenazaquin, pyridaben, tebufenpyrad, tolfenpyrad, flufenerim;

METI II and III compounds: acequinocyl, fluacyprim, hydramethylnon;

Uncouplers: chlorfenapyr;

oxidative phosphorylation inhibitors: cyhexatin, diafenthiuron, fenbutatin oxide, propargite;

moulting disruptor compounds: cryomazine;

mixed function oxidase inhibitors: piperonyl butoxide;

sodium channel blockers: indoxacarb, metaflumizone;

others: benclothiaz, bifenazate, cartap, flonicamid, pyridalyl, pymetrozine, sulfur, thiocyclam, flubendiamide, chlorantraniliprole, cyazypyr (HGW86), cyenopyrafen, flupyrazofos, cyflumetofen, amidoflumet, imicyafos, bistrifluron, and pyrifluquinazon.

In some cases the following insecticides have proven to be particularly useful in combination with the compounds in accordance with the instant invention: abamectin, aldicarb, beta-cyfluthrin, chlorpyrifos-E, clothianidin, cyromazine, deltamethrin, diflubenzuron, emamectin-b, fipronil, gamma-cyhalothrin, imidacloprid, L-cyhalothrin, methiocarb, pymetrozine, rynaxapyr, spinosad, spirodiclofen, spiromesifen, spirotetramate, tebufenozide, tebufenpyrad, tefluthrin, thiamethoxam and thiodicarb. These names are the so called INN designations of the compounds well known to the skilled man in the art.

The compositions comprise at least one compound of formula I in accordance with the instant invention and at least on insecticide compound. However, it is also possible to use more than one of each of these groups of compounds to achieve even better results in certain cases.

Furthermore, the compositions may contain a fungicide in addition to an insecticide; suitable fungicides are those also useful in mixtures of compounds of formula I with fungicides, which constitutes another embodiment of the instant invention described hereinafter.

Fungicides are known to the skilled man and described in the prior art. According to their mode of action, these compounds are categorized as inhibitors of nucleic acid synthesis, uncouplers, inhibitors of AA and protein biosynthesis, inhibitors of mitosis and cell division, respiration inhibitors, inhibitors of ergosterol biosynthesis, inhibitors of melanine biosynthesis, host defence inducers, inhibitors of lipid and membrane synthesis, inhibitors of cell wall synthesis, signal transduction inhibitors, ATP production inhibitors and other known fungicides which have a multisite action mechanism or the mode of action of which has not yet been fully elucidated.

Suitable as well as preferred fungicides for combinations with compounds in accordance with the instant invention are disclosed in WO 2008/152092, to which reference is made in this regard.

Furthermore, the following fungicides may be mentioned as examples for combinations with the compounds in accordance with the present invention (as well for mixtures of the compounds solely with fungicides as well as for mixtures comprisng insecticides and fungicides and a compound in accordance with the present invention.

A) Respiration inhibitors

Inhibitors of complex III at $Q_o$ site (e.g. strobilurins): azoxystrobin, coumethoxystrobin, coumoxystrobin, dimoxystrobin, enestroburin, fenaminstrobin, fenoxystrobin/flufenoxystrobin, fluoxastrobin, kresoxim-methyl, metominostrobin, orysastrobin, picoxystrobin, pyraclostrobin, pyrametostrobin, pyraoxystrobin, trifloxystrobin, 2-[2-(2,5-dimethyl-phenoxymethyl)-phenyl]-3-methoxyacrylic acid methyl ester and 2-(2-(3-(2,6-dichlorophenyl)-1-methyl-allylideneaminooxymethyl)-phenyl)-2-methoxyimino-N-methyl-acetamide, pyribencarb, triclopyricarb/chlorodin-carb, famoxadone, fenamidone;

inhibitors of complex III at $Q_i$ site: cyazofamid, amisulbrom, [(3S,6S,7R,8R)-8-benzyl-3-[(3-acetoxy-4-methoxy-pyridine-2-carbonyl)amino]-6-methyl-4,9-dioxo-1,5-dioxonan-7-yl]2-methylpropanoate, [(3S,6S,7R,8R)-8-benzyl-3-[[3-(acetoxymethoxy)-4-methoxy-pyridine-2-carbonyl]amino]-6-methyl-4,9-dioxo-1,5-dioxonan-7-yl]2-methylpropanoate, [(3S,6S,7R,8R)-8-benzyl-3-[(3-isobutoxycarbonyloxy-4-methoxy-pyridine-2-carbonyl)amino]-6-methyl-4,9-dioxo-1,5-dioxonan-7-yl] 2-methylpropanoate, [(3S,6S,7R,8R)-8-benzyl-3-[[3-(1,3-benzodioxol-5-ylmethoxy)-4-methoxy-pyridine-2-carbonyl]amino]-6-methyl-4,9-dioxo-1,5-dioxonan-7-yl] 2-methylpropanoate; (3S,6S,7R,8R)-3-[[(3-hydroxy-4-methoxy-2-pyridinyl)carbonyl]amino]-6-methyl-4,9-dioxo-8-(phenylmethyl)-1,5-dioxonan-7-yl2-methylpropanoate inhibitors of complex II (e.g. carboxamides): benodanil, bixafen, boscalid, carboxin, fenfuram, fluopyram, flutolanil, fluxapyroxad, furametpyr, isopyrazam, mepronil, oxycarboxin, penflufen, penthiopyrad, sedaxane, tecloftalam, thifluzamide, N-(4'-trifluoromethylthiobiphenyl-2-yl)-3-difluoromethyl-1-methyl-1H-pyrazole-4-carboxamide, N-(2-(1,3,3-trimethyl-butyl)-phenyl)-1,3-dimethyl-5-fluoro-1H-pyrazole-4-carboxamide, N-[9-(dichloromethylene)-1,2,3,4-tetrahydro-1,4-methanonaphthalen-5-yl]-3-(difluoromethyl)-1-methyl-1H-pyrazole-4-carboxamide, 3-(difluoromethyl)-1-methyl-N-(1,1,3-trimethylindan-4-yl)pyrazole-4-carboxamide, 3-(trifluoromethyl)-1-methyl-N-(1,1,3-trimethylindan-4-yl)pyrazole-4-carboxamide, 1,3-dimethyl-N-(1,1,3-trimethylindan-4-yl)pyrazole-4-carboxamide, 3-(trifluoromethyl)-1,5-dimethyl-N-(1,1,3-trimethylindan-4-yl)pyrazole-4-carboxamide, 3-(difluoromethyl)-1,5-dimethyl-N-(1,1,3-trimethylindan-4-yl)pyrazole-4-carboxamide, 1,3,5-tri-methyl-N-(1,1,3-tri-methylindan-4-yl)pyrazole-4-carboxamide;

other respiration inhibitors (e.g. complex I, uncouplers): diflumetorim, (5,8-difluoroquinazolin-4-yl)-{2-[2-fluoro-4-(4-trifluoromethylpyridin-2-yloxy)-phenyl]-ethyl}-amine; nitrophenyl derivates: binapacryl, dinobuton, dinocap, fluazinam; ferimzone; organometal compounds: fentin salts, such as fentin-acetate, fentin chloride or fentin hydroxide; ametoctradin; and silthiofam;

B) Sterol biosynthesis inhibitors (SBI fungicides)

C14 demethylase inhibitors (DMI fungicides): triazoles: azaconazole, bitertanol, bromuconazole, cyproconazole, difenoconazole, diniconazole, diniconazole-M, epoxiconazole, fenbuconazole, fluquinconazole, flusilazole, flutriafol, hexaconazole, imibenconazole, ipconazole, metconazole, myclobutanil, oxpoconazole, paclobutrazole, penconazole, propiconazole, prothioconazole, simeconazole, tebuconazole, tetraconazole, triadimefon, triadimenol, triticonazole, uniconazole, 1-[rel-(2S,3R)-3-(2-chlorophenyl)-2-(2,4-difluorophenyl)-oxiranylmethyl]-5-thiocyanato-1H-[1,2,4]triazole, 2-[rel-(2S,3R)-3-(2-chlorophenyl)-2-(2,4-difluorophenyl)-oxiranylmethyl]-2H-[1,2,4]triazole-3-thiol; imidazoles: imazalil, pefurazoate, prochloraz, triflumizol; pyrimidines, pyridines and piperazines: fenarimol, nuarimol, pyrifenox, triforine;

Delta14-reductase inhibitors: aldimorph, dodemorph, dodemorph-acetate, fenpropimorph, tridemorph, fenpropidin, piperalin, spiroxamine;

Inhibitors of 3-keto reductase: fenhexamid;

C) Nucleic acid synthesis inhibitors phenylamides or acyl amino acid fungicides: benalaxyl, benalaxyl-M, kiralaxyl, metalaxyl, metalaxyl-M (mefenoxam), ofurace, oxadixyl;

others: hymexazole, octhilinone, oxolinic acid, bupirimate, 5-fluorocytosine, 5-fluoro-2-(p-tolylmethoxy)pyrimidin-4-amine, 5-fluoro-2-(4-fluorophenylmethoxy)pyrimidin-4-amine;

D) Inhibitors of cell division and cytoskeleton tubulin inhibitors, such as benzimidazoles, thiophanates: benomyl, carbendazim, fuberidazole, thiabendazole, thiophanate-methyl; triazolopyrimidines: 5-chloro-7-(4-methylpiperidin-1-yl)-6-(2,4,6-trifluorophenyl)-[1,2,4]triazolo[1,5-a]pyrimidine other cell division inhibitors: diethofencarb, ethaboxam, pencycuron, fluopicolide, zoxamide, metrafenone, pyriofenone;

E) Inhibitors of amino acid and protein synthesis methionine synthesis inhibitors (anilino-pyrimidines): cyprodinil, mepanipyrim, pyrimethanil;

protein synthesis inhibitors: blasticidin-S, kasugamycin, kasugamycin hydrochloride-hydrate, mildiomycin, streptomycin, oxytetracyclin, polyoxine, validamycin A;

F) Signal transduction inhibitors

MAP/histidine kinase inhibitors: fluoroimid, iprodione, procymidone, vinclozolin, fenpiclonil, fludioxonil;

G protein inhibitors: quinoxyfen;

G) Lipid and membrane synthesis inhibitors

Phospholipid biosynthesis inhibitors: edifenphos, iprobenfos, pyrazophos, isoprothiolane;

lipid peroxidation: dicloran, quintozene, tecnazene, tioclofos-methyl, biphenyl, chloroneb, etridiazole;

phospholipid biosynthesis and cell wall deposition: dimethomorph, flumorph, mandipropamid, pyrimorph, benthiavalicarb, iprovalicarb, valifenalate and N-(1-(1-(4-cyano-phenyl)ethanesulfonyl)-but-2-yl) carbamic acid-(4-fluorophenyl) ester;

compounds affecting cell membrane permeability and fatty acides: propamocarb, propamocarb-hydrochlorid fatty acid amide hydrolase inhibitors: 1-[4-[4-[5-(2,6-difluorophenyl)-4,5-dihydro-3-isoxazolyl]-2-thiazolyl]-1-piperidinyl]-2-[5-methyl-3-(trifluoromethyl)-1H-pyrazol-1-yl]ethanone H) Inhibitors with Multi Site Action inorganic active substances: Bordeaux mixture, copper acetate, copper hydroxide, copper oxychloride, basic copper sulfate, sulfur;

thio- and dithiocarbamates: ferbam, mancozeb, maneb, metam, metiram, propineb, thiram, zineb, ziram;

organochlorine compounds (e.g. phthalimides, sulfamides, chloronitriles): anilazine, chlorothalonil, captafol, captan, folpet, dichlofluanid, dichlorophen, flusulfamide, hexachlorobenzene, pentachlorphenole and its salts, phthalide, tolyifluanid, N-(4-chloro-2-nitro-phenyl)-N-ethyl-4-methyl-benzenesulfonamide;

guanidines and others: guanidine, dodine, dodine free base, guazatine, guazatine-acetate, iminoctadine, iminoctadine-triacetate, iminoctadine-tris(albesilate), dithianon, 2,6-dimethyl-1H,5H-[1,4]dithiino[2,3-c:5,6-c']dipyrrole-1,3,5,7 (2H,6H)-tetraone;

I) Cell wall synthesis inhibitors inhibitors of glucan synthesis: validamycin, polyoxin B; melanin synthesis inhibitors: pyroquilon, tricyclazole, carpropamid, dicyclomet, fenoxanil;

J) Plant defence inducers acibenzolar-S-methyl, probenazole, isotianil, tiadinil, phosphonates: fosetyl, fosetyl-aluminum, phosphorous acid and its salts;

K) Unknown mode of action bronopol, chinomethionat, cyflufenamid, cymoxanil, dazomet, debacarb, diclomezine, difenzoquat, difenzoquat-methylsulfate, diphenylamin, fenpyrazamine, flumetover, flusulfamide, flutianil, methasulfocarb, nitrapyrin, nitrothalisopropyl, oxin-copper, proquinazid, tebufloquin, teclofталат, triazoxide, 2-butoxy-6-iodo-3-propylchromen-4-one, N-(cyclo-propylmethoxyimino-(6-difluoro-methoxy-2,3-difluoro-phenyl)-methyl)-2-phenyl acetamide, N'-(4-(4-chloro-3-trifluoromethyl-phenoxy)-2,5-dimethyl-phenyl)-N-ethyl-N-methyl formamidine, N'-(4-(4-fluoro-3-trifluoromethyl-phenoxy)-2,5-dimethyl-phenyl)-N-ethyl-N-methyl formamidine, N'-(2-methyl-5-trifluoromethyl-4-(3-trimethylsilanyl-propoxy)-phenyl)-N-ethyl-N-methyl formamidine, N'-(5-difluoromethyl-2-methyl-4-(3-trimethylsilanyl-propoxy)-phenyl)-N-ethyl-N-methyl formamidine, 2-{1-[2-(5-methyl-3-trifluoromethyl-pyrazole-1-yl)-acetyl]-piperidin-4-yl}-thiazole-4-carboxylic acid methyl-(1,2,3,4-tetrahydro-naphthalen-1-yl)-amide, 2-{1-[2-(5-methyl-3-trifluoromethyl-pyrazole-1-yl)-acetyl]-piperidin-4-yl}-thiazole-4-carboxylic acid methyl-(R)-1,2,3,4-tetrahydro-naphthalen-1-yl-amide, 1-[4-[4-[5-(2,6-difluorophenyl)-4,5-dihydro-3-isoxazolyl]-2-thiazolyl]-1-piperidinyl]-2-[5-methyl-3-(trifluoromethyl)-1H-pyrazol-1-yl]ethanone, methoxy-acetic acid 6-tert-butyl-8-fluoro-2,3-dimethyl-quinolin-4-yl ester, N-Methyl-2-{1-[(5-methyl-3-trifluoromethyl-1H-pyrazol-1-yl)-acetyl]-piperidin-4-yl}-N-[(1R)-1,2,3,4-tetrahydronaphthalen-1-yl]-4-thiazolecarboxamide,3-[5-(4-methylphenyl)-2,3-dimethyl-isoxazolidin-3-yl]-pyridine, 3-[5-(4-chloro-phenyl)-2,3-dimethyl-isoxazolidin-3-yl]-pyridine (pyrisoxazole), N-(6-methoxy-pyridin-3-yl) cyclopropanecarboxylic acid amide, 5-chloro-1-(4,6-dimethoxy-pyrimidin-2-yl)-2-methyl-1H-benzoimidazole, 2-(4-chloro-phenyl)-N-[4-(3,4-dimethoxy-phenyl)-isoxazol-5-yl]-2-prop-2-ynyloxy-acetamide;

L) Antifungal biocontrol agents, plant bioactivators: *Ampelomyces quisqualis* (e.g. AQ 10® from Intrachem Bio GmbH & Co. KG, Germany), *Aspergillus flavus* (e.g. AFLA-GUARD® from Syngenta, CH), *Aureobasidium pullulans* (e.g. BOTECTOR® from bio-ferm GmbH, Germany), *Bacillus pumilus* (e.g. NRRL Accession No. B-30087 in SONATA® and BALLAD® Plus from AgraQuest Inc., USA), *Bacillus subtilis* (e.g. isolate NRRL-Nr. B-21661 in RHAPSODY®, SERENADE® MAX and SERENADE® ASO from AgraQuest Inc., USA), *Bacillus subtilis* var. *amyliquefaciens* FZB24 (e.g. TAEGRO® from Novozyme Biologicals, Inc., USA), *Candida oleophila* I-82 (e.g. ASPIRE® from Ecogen Inc., USA), *Candida saitoana* (e.g. BIOCURE® (in mixture with lysozyme) and BIOCOAT® from Micro Flo Company, USA (BASF SE) and Arysta), Chitosan (e.g. ARMOUR-ZEN from BotriZen Ltd., NZ), *Clonostachys rosea* f. *catenulata*, also named *Gliocladium catenulatum* (e.g. isolate J1446: PRESTOP® from Verdera, Finland), *Coniothyrium minitans* (e.g. CONTANS® from Prophyta, Germany), *Cryphonectria parasitica* (e.g. *Endothia parasitica* from CNICM, France), *Cryptococcus albidus* (e.g. YIELD PLUS® from Anchor Bio-Technologies, South Africa), *Fusarium oxysporum* (e.g. BIOFOX® from S.I.A.P.A., Italy, FUSACLEAN® from Natural Plant Protection, France), *Metschnikowia fructicola* (e.g. SHEMER® from Agrogreen, Israel), *Microdochium dimerum* (e.g. ANTI-BOT® from Agrauxine, France), *Phlebiopsis gigantea* (e.g. ROTSOP® from Verdera, Finland), *Pseudozyma flocculosa* (e.g. SPORODEX® from Plant Products Co. Ltd., Canada), *Pythium oligandrum* DV74 (e.g. POLYVERSUM® from Remeslo SSRO, Biopreparaty, Czech Rep.), *Reynoutria sachlinensis* (e.g. REGALIA® from Marrone Biolnnovations, USA), *Talaromyces flavus* V117b (e.g. PROTUS® from Prophyta, Germany), *Trichoderma asperellum* SKT-1 (e.g. ECO-HOPE® from Kumiai Chemical Industry Co., Ltd., Japan), *T. atroviride* LC52 (e.g. SENTINEL® from Agrimm Technologies Ltd, NZ), *T. harzianum* T-22 (e.g. PLANTSHIELD® der Firma BioWorks Inc., USA), *T. harzianum* TH 35 (e.g. ROOT PRO® from Mycontrol Ltd., Israel), *T. harzianum* T-39 (e.g. TRICHODEX® and TRICHODERMA 2000® from Mycontrol Ltd., Israel and Makhteshim Ltd., Israel), *T. harzianum* and *T. viride* (e.g. TRICHOPEL from Agrimm Technologies Ltd, NZ), *T. harzianum* ICC012 and *T. viride* ICC080 (e.g. REMEDIER® WP from Isagro Ricerca, Italy), *T. polysporum* and *T. harzianum* (e.g. BINAB® from BINAB Bio-Innovation AB, Sweden), *T. stromaticum* (e.g. TRICOVAB® from C.E.P.L.A.C., Brazil), *T. virens* GL-21 (e.g. SOILGARD® from Certis LLC, USA), *T. viride* (e.g. TRIECO® from Ecosense Labs. (India) Pvt. Ltd., Indien, BIO-CURE® F from T. Stanes & Co. Ltd., Indien), *T. viride* TV1 (e.g. *T. viride* TV1 from Agribiotec srl, Italy), *Ulocladium oudemansii* HRU3 (e.g. BOTRY-ZEN® from Botry-Zen Ltd, NZ)

The following fungicides have proved advantageous in certain applications:

N-(2-(1,3-dimethylbutyl)phenyl)-5-fluoro-1,3-dimethyl-1H-pyrazole-4-carboxamide, metalaxyl, carbendazim, pencycuron, fenamidone, fluoxastrobin, pyrimethanil, iprodione, bitertanolo, fluquinconazole, ipconazole, prochloraz, epoxyconazole, prothioconazole, tebuconazole, triadimenol, tritiсonazole, carpropamid, tolylfluanid, fluopicolide, isotianil, N-(2-(1,1'-bi(cyclopropyl)-2-yl)phenyl-3-difluoromethyl)-1-methyl-1H-pyrazole-4-carboxamide, propamocarb, fosetylate, N-(2-(3-chloro)-5-trifluormethyl)-pyridin-2-yl)

ethyl)-2-(trifluoromethyl)benzamide, fludioxonil, mefenoxam, pyraclostrobin, boscalid and azoxystrobin and mixtures thereof.

The compositions may contain one of more fungicides and one or more compounds of formula I in accordance with the instant invention.

It has furthermore been found that the compounds in accordance with the instant invention may also combined with known herbicides to provide compositions having increased efficacy in combating weeds compared to either the activity of the known herbicide or the efficacy of the compound of formula I. Suitable herbicides are known to the skilled person and described in the literature.

The compositions in accordance with the instant invention may further comprise additional components such as carriers, supports, fillers, surfactants, protective colloids, adhesives, thickeners, stabilisers, thixotropic agents, penetration agents or sequestering agents. In general any additive may be contained which complies with the usual formulation techniques applied by the skilled persons in the preparation of respective compositions. Examples for such additives are given in WO 2008/152091 or WO 2008/152092 to which reference is made for further details.

Without being specifically limited, the compositions in accordance with the instant invention usually contain between 0.5 and 99% by weight of compounds of formula I and other active ingredients together, preferably of from 10 to 90% by weight.

The compositions in accordance with the instant inventions may be used in a variety of forms known to the skilled person in the art of formulation of insecticidal or fungicidal compositions. Again, details of such forms are given in WO 2008/152091 or WO 2008/152092 to which reference is made for further details.

Details of methods for curatively or preventively controlling insects and/or fungi and/or increasing the yield, growth or vigor of a plant applying a composition in accordance with the instant invention via seed treatment, foliar application, stem application, drench/drip application, to the seed, the plant or the soil are also given in WO 2008/152091 or WO 2008/152092.

The compositions in accordance with the instant invention are well tolerated by plants and are environmentally friendly. Thus, the compositions are suitable for improving the quality of the harvested material and for controlling animal pests encountered in agriculture, in forests, in gardens and leisure facilities, in the protection of stored products and in the hygiene sector.

The following examples show preferred embodiments of the instant invention without limiting the scope thereof in accordance with the claims.

The analytical methods referred to in the Examples were used as set forth below:

NMR spectroscopy

For NMR analyses, a sample containing about 350 µg of the isolated PsCCD7/8 product were dissolved in 500 µL of CD2Cl2. The NMR experiments were performed on a Bruker AVANCE II spectrometer operation at a 1H resonance frequency of 400.13 MHz. The instrument was equipped with a 5 mm dual probe (BBI) for inverse detection with a z-gradient coil and with pulse angles of 6.5 µs ($^1H$) and 13 µs ($^{13}C$) respectively. Bruker TOPSPIN software (version 2.1, patch level 2) was used to acquire and process the NMR data. The measurements were carried out at room temperature (298 K) with the exception of the DOSY experiment measured at 303 K (temperature controlled).

For the 1D $^1H$ experiment, the parameters were as follows: standard one-pulse experiment (zg), 32 transients, a spectral width of 9 ppm, a data size of 32K points, a relaxation delay 5 s, an acquisition time of 4.55 s were used. For 2D $^1H$—$^1H$-COSY the gradient-enhanced COSY experiment for magnitude mode of detection (cosygqf), 32 scans, a relaxation delay of 1 s, an acquisition time of 0.57 s, a spectral width in both dimensions (f2, f1) of 9 ppm, 4096 and 512 acquired data points in f2 and f1 respectively were used. Data were processed by zero filling (to 1024) in f1 and by using unshifted squared sine window functions in both dimensions prior to 2D Fourier transformation.

For 2D $^1H$—$^{13}C$-HSQC, the gradient-enhanced HSQC experiment with carbon multiplicity editing and echo-antiecho acquisition mode (hsqcedetgpsisp2.2), 64 transients, a relaxation time of 1.5 s, an acquisition time of 0.28 s, spectral widths of 9 ppm and 170 ppm (in f2 and f1), with 2048 and 512 acquired data points respectively, were used. Data were processed by zero-filling (to 1024) and linear prediction in f1, and by using shifted squared sine window functions in both dimensions prior to Fourier transformation.

For 2D $^1H$—$^{13}C$-HMBC, the gradient-enhanced HMBC experiment with twofold low-pass J-filter to suppress one-bond correlations and echo-antiecho acquisition mode (hmbcetgpl2nd), 80 transients, a relaxation time of 1 s, an acquisition time of 0.28 s, spectral widths (in f2 and f1) of 9 ppm and 200 ppm with 2048 and 512 acquired data points respectively, were used. Data were processed by zero-filling (to 1024) and linear prediction in f1 and by using shifted squared sine window functions in both dimensions prior to Fourier transformation.

For 1D $^1H$—{$^1H$—}-NOE, the standard 1D NOE experiment using the second channel for selective irradiation of selected target protons (zgf2pr) was applied. For averaging unwanted long-term effects eightfold cycling through the frequency list, with the acquisition of 8×32 transients for the individual subspectra was performed. A spectral width of 9 ppm, a data size of 32K points, a relaxation and preirradiation delay of 3 s, and an acquisition time of 4.55 s were used.

$^1H$ and $^{13}C$ chemical shift prediction was performed using the ACD (Advanced Chemistry Development, Inc.) software, release 11.00 version 11.02 (2008).

Enzymatic assays with crude and purified protein

Substrates were purified using thin-layer silica gel plates (Merck, Darmstadt, Germany). Plates were developed in light petroleum/diethylether/acetone (40:10:10 v/v/v). Substrates were scraped off in dim daylight and eluted with acetone. β-carotene was obtained from Roth (Karlsruhe, Germany). 9-cis-β-carotene, 13-cis-β-carotene and 15-cis-β-carotene were obtained from carotenature (Lupsingen, Switzerland).

Standard in vitro assays were performed in a total volume of 200 µl. 50 µl of substrates (160 µM) in ethanol were mixed with 50 µl of ethanolic Triton X-100 (0.8%, v/v; Sigma, Deisenhofen, Germany), dried using a vacuum centrifuge and then resuspended in 50 µl water. The prepared substrates were then mixed with 100 µl of 2 X incubation buffer containing 2 mM TCEP, 0.4 mM FeSO4, 200 mM Hepes-NaOH pH 8 and 2 mg/ml catalase (Sigma, Deisenhofen, Germany). Purified Protein was then added to a final concentration of 400 ng/µl. Crude assays were performed using 50 µl of the soluble fractions of overexpressing cells. The assays were incubated for 2 h at 28° C. Extraction was done by adding two volumes of each acetone and light petroleum/diethylether (1:4 v/v). After centrifugation, the epiphase was collected.

CCD7/CCD8 double assays were performed in a total volume of 200 µl. 50 µl of substrates (320 µM) in EtOH were mixed with 50 µl of ethanolic Triton X-100 (0.8%, v/v;

Sigma, Deisenhofen, Germany), dried using a vacuum centrifuge and then resuspended in 100 µl of 2 X incubation buffer containing 2 mM TCEP, 0.4 mM FeSO4, 200mM Hepes-NaOH pH 7.8 and 2 mg/ml catalase (Sigma, Deisenhofen, Germany). Purified Protein was then added to a final concentration of 200 ng/µl. Crude assays were performed using each 40 µl of the soluble fractions of overexpressing cells. The assays were incubated for 3 h at 28° C. Extraction was done by adding two volumes of each acetone and light petroleum/diethylether (1:4, v/v). After centrifugation, the epiphase was collected.

EXAMPLE 1

Biochemical Synthesis of Compound IA

In vitro incubation of CCD8 enzymes with 9-cis-β-apo-10'-carotenal resulted in a novel compound exhibiting an absorption maximum at around 268 nm (the starting material has an absorption maximum at appr. 447 nm), which was further analyzed after purification through two different HPLC separation systems. Combined assays with a combination of CCD7 and CCD8 enzymes and using 9-cis-β-carotene as substrate led to the same novel compound.

The purification of the novel compound by preparative HPLC was carried out as follows:

A Waters system equipped with a photodiode array detector (model 996) was used to purify the PsCCD7/PsCCD8 product. The purification step was performed using a YMC-Pack C30-reversed phase column (250×4.6 mm i.d., 5 µm; YMC Europe, Schermbeck, Germany) with the solvent systems B: methanol/water/tert-butylmethyl ether (60:20:2 v/v/v) and A: methanol/tert-butylmethyl ether (50:50 v/v). The column was developed at a flow-rate of 1 ml/min with a gradient from 100% B to 80% B within 15 min, then to 0% B within 0.5 min and finally to 0% B and a flow-rate of 2 m/min within 0.5 min, maintaining the final conditions for another 14 min. The collected fractions were dried using a rotary evaporator and resolved in methanol. The second purification step was performed using a MN Nucleosil 100 C18-reversed phase column (250×4 mm i.d., 10 µm; Macherey-Nagel, Duren, Germany) with the solvent systems B: methanol/water (20:80 v/v) and A: methanol. The column was developed for 8 min with solvent B at a flow-rate of 1 ml/min, followed by a linear gradient from 100% B to 100% A within 1 min, maintaining the final conditions for another 10 min.For structure determination of the novel compound, various NMR techniques were applied.

350 µg of the purified novel compound were dissolved in $CD_2Cl_2$ and subjected to 1D $^1H$, 1D $^1H(^1H)$ NOE and three different 2D NMR techniques (2D $^1H$—$^1H$-COSY, 2D $^1H$-$^{13}C$ heteronuclear single quantum coherence and 2D $^1H$—$^{13}C$ heteronuclear multiple bond spectrometry). The 1D NOE experiment was used to detect spatial proximity among protons. The 2D $^1H$—$^1H$-COSY experiment was applied for unraveling the homo-nuclear coupling network and for assigning the corresponding $^1H$ signals to the individual protons. Taking advantage of the 2D $^1H$—$^{13}C$-heteronuclear single quantum coherence (HSQC) experiment dedicated for detecting one-bond ($^1J_{CH}$) spin-spin interactions and its ability to differentiate among different carbon types (CH$_3$, CH$_2$, CH), these $^1H$ signals were correlated with the $^{13}C$ signals of directly bound carbons. The 2D $^1H$-$^{13}C$-heteronuclear multiple bond correlation (HMBC) experiment, which detects long-range couplings between protons and carbons connected through two or three bonds ($^{2,3}J_{CH}$), served to assign the signals of quaternary carbons and to independently prove the assignments of the proton-bearing carbons. The analysis of the results allowed the unequivocal assignment of the structure of formula IA to the novel compound. These results were confirmed through high resolution mass spectrometry yielding the composition $C_{19}H_{26}O_3$ and through UV spectroscopy indicating a maximum of three conjugated double bonds.

EXAMPLE 2

Isomerization Function of DWARF27

OsDWARF27 (an enzyme in rice) was expressed in fusion with thioredoxin and in vitro assays were performed with all-trans-β-carotene, using crude lysate of transformed E. coli cells. HPLC analysis revealed the conversion of the substrate into its 9-cis-isomer confirmed by comparison with an authentic standard. In addition, combined incubation of DWARF27 CCD7 and CCD8 with all-trans-β-carotene led to the novel compound of formula IA as obtained in Example 1 while controls performed with DWARF27 or with CCD7 and CCD8 did not show the formation of this compound.

This result confirmed the enzymatic function of DWARF27 which was hitherto unclear, namely as an isomerase for all-trans carotenes to the respective cis-carotenes, in particular to form 9-cis-β-carotene from all-trans-β-carotene.

EXAMPLE 3

Biological Activity of the Compound of Formula IA (as Characterized in Example 1)

Striga Seed Germination Assay

Pre-conditioning of Striga hermonthica seeds was carried out in a first step to see the effect of germination stimulants. For this purpose clean Striga seeds were surface sterilized with 2% sodium hypochlorite in sterile water containing 0.4% of Tween-20. About 50 to 100 sterilized seeds were spread on 9-mm diameter glass fibre filter paper discs. Twelve of these discs were placed in a 9-cm diameter Petri-dish on sterilized Whatman filter paper, moistened with 3.0 ml sterilized water. After sealing with parafilm, the Petri-dishes were placed in darkness in an incubator at 30° C. After 10 days of incubation, the discs with preconditioned seeds were supposed to be ready to test germination stimulant. Surplus moisture was evaporated from each petri dish in laminar flow cabinet. The dry discs were then placed in another Petri-dish (six per Petri-dish) containing a filter paper ring (outer diameter 9 cm, inner diameter 8 cm) moistened with 0.9 ml water. Various concentration of the compound of formula IA were applied (50 µl per disc) to triplicate discs. GR24 a synthetic strigolactone analogue, was applied as positive control. Subsequently, the Striga seeds were incubated in darkness at 30° C. for another 48 hours and germination (seeds with radicle protruding through the seed coat) scored with the help of a binocular microscope.

The compound of formula IA as obtained in Example in concentrations of from 0.03 to 330 µM resulted in germination of the seeds in the range of from 2 to 62%, which is an activity in this regard of the same order of magnitude as the known synthetic strigolactone analogue GR 24 which yielded a germination activity of appr. 50% at a concentration of 3.3 µM under the same conditions.

This result shows that compound IA can be used for germination of Striga varieties.

Rice Tillering Assay

Rice seeds were surface sterilized with 2% sodium hypochlorite. The seeds were allowed to germinate in a Petri dish on a moistened filter paper. In the meanwhile bottom of 1.5 ml eppendorf tube was cut and filled with 0.6% phytoagar. One pre-germinated seed was planted in the center of the tube on solid phytoagar and this tube was fitted in the cap of 10 ml plastic tube. The 10 ml tube was filled with modified Hoagland nutrient solution. After two weeks of planting, the compound of formula IA (2 μM) was added through nutrient solution to half of the tubes of each rice cultivars/mutants and the remaining half were kept as control. The nutrient solution with or without the compound of formula IA was supplied daily. Number of tillers per plant was counted at 24 hours interval up to 12 days of carlactone application.

In addition to its activity in inducing seed germination of parasitic plants, the compound of formula IA also exerted the function of strigolactone in regulating tillering of rice. Treatment with this compound led to a reduction of tiller number of the ccd8 rice mutant (d10) comparable to that shown by the strigolactone analogue GR24.

The results of the foregoing examples show that the novel compounds in accordance with the instant invention can replace strigolactones in a number of interesting applications.

The invention claimed is:

1. A compound of general formula I:

(I)

wherein:
$R^a$ is hydrogen;
$R^b$ is hydrogen;
$R^c$ is $C_1$-$C_8$ alkyl,
$R^f$ is hydrogen;
$R^d$ is $C_1$-$C_8$ alkyl, wherein the hydrogen atoms of the alkyl may be partly replaced by other groups or atoms;
$R^e$ represents a substituent $R^1$ which represents $C_1$-$C_8$-alkyl, $C_2$-$C_8$ alkenyl, $C_2$-$C_8$-alkinyl, $C_3$-$C_8$-cycloalkyl or $C_1$-$C_8$-alkoxy, in each of which the hydrogen atoms may be partly replaced by other groups or atoms; or —CH=CH—$R^7$, wherein $R^7$ represents a hydrogen atom, $C_1$-$C_8$-alkyl or a 4-, 5- 6- or 7-membered saturated or unsaturated, aromatic or non-aromatic carbocyclic or heterocyclic ring or a fused ring system containing more than one of those rings.

2. A compound in accordance with claim 1, wherein $R^c$ is a $C_1$-$C_4$ alkyl group.

3. A compound in accordance with claim 1, wherein $R^c$ is methyl.

4. A compound in accordance with claim 1, wherein $R^d$ is methyl.

5. A compound in accordance with claim 1, wherein $R^c$ is methyl and $R^d$ is methyl.

6. A compound in accordance with claim 1, wherein $R^e$ is represented by —CH=CH—$R^7$, wherein $R^7$ represents a hydrogen atom, $C_1$-$C_8$-alkyl or a 4-, 5- 6- or 7-membered saturated or unsaturated, aromatic or non-aromatic carbocyclic or heterocyclic ring, or a fused ring system containing more than one of those rings.

7. A compound in accordance with claim 1, wherein $R^e$ is represented by —CH=CH—$R^7$, wherein $R^7$ is a five- or six-membered carbocyclic ring which may be saturated or unsaturated.

8. A compound in accordance with claim 1, wherein $R^e$ is represented by —CH=CH—$R^7$, wherein $R^7$ is represented by a cyclohexenyl ring which may be substituted.

9. A compound in accordance with claim 1, wherein $R^e$ is represented by —CH=CH—$R^7$, wherein $R^7$ is represented by a cyclohexenyl ring which is substituted with a hydroxyl group, a $C_1$-$C_8$ alkyl, a $C_1$-$C_8$ alkoxy, or acetyl group.

10. A compound in accordance with claim 1, wherein $R^e$ represents a $C_1$-$C_8$ alkyl or a $C_2$-$C_8$ alkenyl group, optionally substituted with a hydroxyl group or a carbonyl group or a cycloalkyl group which itself might be substituted.

11. A composition comprising at least one compound according to claim 1 and also at least one insecticide, fungicide, or herbicide.

12. A method for controlling the germination of parasitic root plants, wherein a compound is used as a germination trap in which the compound is represented by the following:

(I)

wherein $R^a$, $R^b$ and $R^c$, independently from each other, represent:
a hydrogen atom, a halogen atom, a nitro group, a cyano group, a formyloxy group, a formylamino group or a carbamate group,
a substituent $R^1$, wherein $R^1$ represents $C_1$-$C_8$-alkyl-, $C_2$-$C_8$ alkenyl, $C_2$-$C_8$-alkinyl, $C_3$-$C^8$-cycloalkyl or $C_1$-$C_8$-alkoxy, in each of which the hydrogen atoms may be partly replaced by other groups or atoms,
a substituent —$OR^2$, wherein $R^2$ represents a hydrogen atom, $C_1$-$C_8$ alkyl, $C_2$-$C_8$alkenyl, $C_2$-$C_8$-alkinyl, $C_1$-$C_8$-alkylcarbonyl, $C_1$-$C_8$-alkylaminocarbonyl, or $C_1$-$C_8$-alkoxycarbonyl, in each of which the hydrogen atoms may be partly replaced by other groups or atoms
a substituent —$NR^3R^4$, wherein $R^3$ and $R^4$, independently from each other, represent a hydrogen atom, $C_1$-$C_8$ alkyl, $C_1$-$C_8$-alkylcarbonyl, $C_1$-$C_8$-halogenoalkylcarbonyl, phenyl or benzyl, in each of which the hydrogen atoms may be partly replaced by other groups or atoms,
a substituent —C(O)—$R^5$, wherein $R^5$ represents a hydrogen atom, $C_1$-$C_8$-alkyl or $C_1$-$C_8$-alkyloxy, in each of which the hydrogen atoms may be partly replaced by other groups or atoms,—NH2, NHR$^5$ or NR$^5$R$^5$ (where the two substituents R$^5$ may be the same or different), —NR$^5$(OH),
a substituent —S(O)n-R$^6$, wherein n is 0, 1 or 2 and R6 represents $C_1$-$C_8$-alkyl in which the hydrogen atoms may be partly replaced by other groups or atoms, —NH$_2$, —NHR$^6$ or NR$^6$R$^6$(where the two substituents R$^6$ may be the same or different), or a 4-, 5-, 6- or 7-membered heterocyclic ring comprising up to 4 heteroatoms selected from nitrogen, oxygen or sulfur, where in each of these rings the hydrogen atoms may be partly replaced by other groups or atoms, $R^d$ represents $C_1$-$C_8$ alkyl, $C_2$-$C_8$-alkenyl or $C_2$-$C_8$-alkinyl, wherein the hydrogen atoms may be partly replaced by other groups or atoms, $R^e$ represents a substituent $R^1$ as defined above, or —CH=CH-$R^7$, wherein $R^7$ represents a hydrogen atom, $C_1$-$C_8$-alkyl or a 4-, 5- 6- or 7-membered saturated or unsaturated, aromatic or non-aromatic carbocyclic or heterocyclic ring or a fused ring system containing more than one of those rings $R^d$ and $R^e$ together form a 4-,5-6- or 7-membered saturated or unsaturated, aromatic or non-aromatic carbocyclic or heterocyclic ring, which may be fused to another saturated or unsaturated, aromatic or non-aromatic carload ie or heterocyclic ring with the proviso that the carbon atom carrying substituents $R^d$ and $R^e$ is not part of an enone-structural element, and

$R^f$ represents a hydrogen atom, halogen atom, a nitro group, a cyano group or $C_1$-$C_8$-alkyl-, $C_2$-$C_8$ alkenyl, $C_2$-$C_8$-alkinyl or $C_3$-$C_8$-cycloalkyl.

13. A method according to claim 12, wherein for the compound of formula I $R^a$ and $R^b$ are hydrogen and $R^c$ is a substituent $R^1$.

14. A method according to claim 12, wherein the $R^c$ is $C_1$-$C_8$-alkyl.

15. A method according to claim 12, the compound is represented by one of the following formulae:

16. A method according to claim 12, wherein the compound is represented by formula IA:

(IA)

17. The method of claim 12, wherein the compound is a compound according to claim 1.

18. The method of claim 12, wherein the parasitic root plant is a parasitic weed.

19. The method according to claim 12, wherein the parasitic root plant is a *Striga* or a *Orobanche* plant.

* * * * *